United States Patent [19]
Frisch et al.

[11] Patent Number: 5,846,905
[45] Date of Patent: *Dec. 8, 1998

[54] OIL-IN-WATER EMULSIONS

[75] Inventors: Gerhard Frisch, Wehrheim; Zoltan Damo, Eppstein, both of Germany

[73] Assignee: Clariant GmbH, Germany

[ * ] Notice: The term of this patent shall not extend beyond the expiration date of Pat. No. 5,700,472.

[21] Appl. No.: 663,286

[22] PCT Filed: Dec. 14, 1994

[86] PCT No.: PCT/EP94/04141

§ 371 Date: Aug. 29, 1996

§ 102(e) Date: Aug. 29, 1996

[87] PCT Pub. No.: WO95/17087

PCT Pub. Date: Jun. 29, 1995

[30] Foreign Application Priority Data

Dec. 22, 1993 [DE] Germany .......................... 43 43 856.3

[51] Int. Cl.⁶ .......................... A01N 25/04; A01N 57/00; A61K 9/07; B01J 13/00
[52] U.S. Cl. ...................... 504/116; 71/DIG. 1; 252/312; 424/405; 514/86; 514/941; 514/975
[58] Field of Search .......................... 252/312; 71/DIG. 1; 424/405; 514/941, 975, 86; 504/116

[56] References Cited

U.S. PATENT DOCUMENTS

| | | |
|---|---|---|
| 3,074,791 | 1/1963 | Scoles . |
| 3,185,562 | 5/1965 | Scoles et al. . |
| 3,212,967 | 10/1965 | McFadden et al. . |
| 3,740,201 | 6/1973 | Woodruff . |
| 3,948,636 | 4/1976 | Marks ................................. 71/DIG. 1 |
| 4,107,302 | 8/1978 | Watanabe . |
| 4,770,694 | 9/1988 | Iwasaki et al. ....................... 71/DIG. 1 |
| 4,824,663 | 4/1989 | Wirth et al. .......................... 252/312 X |
| 4,851,217 | 7/1989 | Mente et al. . |
| 4,870,103 | 9/1989 | Röchling et al. ........................ 514/521 |
| 4,931,086 | 6/1990 | Moucharafieh ....................... 71/DIG. 1 |
| 4,966,621 | 10/1990 | Heinrich et al. . |
| 5,227,402 | 7/1993 | Röchling et al. ........................ 514/521 |
| 5,700,472 | 12/1997 | Frisch et al. ............................ 424/405 |

FOREIGN PATENT DOCUMENTS

| | | |
|---|---|---|
| 0196463 | 10/1986 | European Pat. Off. . |
| 0289909 | 11/1988 | European Pat. Off. . |
| 0224846 | 10/1990 | European Pat. Off. . |
| 0118759 | 5/1991 | European Pat. Off. . |
| 0499587 | 8/1992 | European Pat. Off. . |
| 2452250 | 10/1986 | France . |
| 3624910 | 1/1988 | Germany . |
| 94-10839 | 5/1994 | WIPO . |

*Primary Examiner*—Richard D. Lovering
*Attorney, Agent, or Firm*—Connolly & Hutz

[57] ABSTRACT

The present invention relates to oil-in-water emulsions containing 0.001–70% by weight of at least one active substance from the group consisting of phosphates, thiophosphates and/or carbamates, 0.001–30% by weight of one or more surfactant compounds from the group consisting of nonionic surfactant compounds or phosphorylated surfactant compounds or sulfated surfactant compounds or sulfonated surfactant compounds, and also, if desired, adjuvants, and, water to make up 100% by weight.

20 Claims, No Drawings

OIL-IN-WATER EMULSIONS

This application is a 371 of PCT/EP94/04141, filed Dec. 14, 1994, published as WO95/17087, Jun. 29, 1995.

Numerous aqueous emulsions of agrochemical active substances have already been disclosed. Such formulations can be prepared, for example, by dissolving the active substances, which are generally insoluble in water, in organic solvents and adding emulsifiers and adjuvants, the active substances, emulsifiers and adjuvants being added in quantities such that sufficiently stable emulsions are formed when the compositions are formulated with water to the application concentrations.

The prior art has disclosed oil-in-water emulsions which contain phosphorylated surfactants.

EP-A-0 224 846 describes plant protection agents based on aqueous emulsions which contain the active substance and, as dispersant, an alpha- and omega-phosphorylated ethylene oxide/propylene oxide/ethylene oxide block copolymer or a salt thereof.

A disadvantage of the emulsions described is that they are only substantially free of water-immiscible organic solvents.

EP-A-0 118 759 discloses plant protection agents in the form of aqueous emulsion concentrates which contain one or more liquid or dissolved active substances, water and, as oil- and water-soluble dispersants, from 0.5 to 20% by weight of salts of phosphorylated block copolymers based on propylene oxide (PO) and ethylene oxide (EO), of the formula

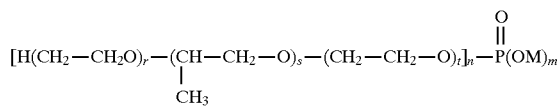

in which r and s independently of one another are a number between 20 and 300, t is a number between 10 and 300, n and m independently of one another are 1 or 2, the sum n+m necessarily being 3, and M is an alkali metal cation, one equivalent of an alkaline earth metal cation, ammonium, alkylammonium or alkanolanmionium.

The only active substances which are mentioned as being suitable are hydrolysis-resistant insecticides, herbicides and pheromones.

U.S. Pat. No. 4,107,302 relates to aqueous insecticide concentrate mixtures which contain an active substance from the group consisting of phosphates and/or thiophosphates, and a surface-active compound. As nonionic surface-active compounds, ethoxylated alkylallylphenyl ethers are preferably employed, for example distyrylmethylphenol ethoxylate with 10 EO. A disadvantage of the mixtures described,,therein is the need to use an aqueous buffer solution in order to establish a pH range of from 3.0 to 8.5. Moreover, the addition of organic solvents such as ketones, ethers and alcohols is recommended for mixtures whose content of active substance exceeds 30% by weight.

EP-A-0 196 469 relates to phosphate-containing macroemulsions where the surfactant employed to disperse the active substance is the aqueous solution of a nonylphenol-propylene oxide-ethylene oxide adduct and/or the aqueous solution of an ethylene oxide/propylene oxide/ethylene oxide block copolymer having an average molecular weight of between 2000 and 8000 and HLB values of between 8 and 30. The macroemulsions described necessarily contain glycerol as adjuvant. When employing an active substance which is solid at room temperature, a solution of the substance concerned in an aromatic diluent is used.

EP-A-0 130 370 relates to plant protection agent combinations which are obtained by mixing a dispersion of active substance and a solution of active substance. The plant protection agent combinations prepared in this way contain as phosphorylated surfactants, for example, the Na salt of $C_{12}$–$C_{18}$-alkyl polyglycol ether phosphate mono/diester (®Forlanit P, Henkel KGaA) and triethanolamide salts of a mixture of mono- and diphosylates of a tristyrylphenol polyglycol ether having 18 EO units (®Soprophor FI, Rhône-Poulenc) and, as sulfated and sulfonated surfactant compounds, for example, the Na salt of the sulfosuccinic monoester and Na ligninsulfonate. A disadvantage of the plant protection agent combinations described therein is the use of solutions of active substances, which have a high content (40–48% by weight) of organic solvents such as xylene and methylnaphthalene.

Oil-in-water emulsions which contain nonionic surfactants as dispersants are likewise known from the prior art.

EP-A-0 289 909 relates to stable aqueous emulsions of organophosphorus pesticides which in addition to the active substance contain a nonionic block copolymer, copolymer or coblock copolymer as surfactant and also, necessarily, urea, so as to achieve an adequate degree of phase stabilization.

A series of further publications from the prior art relates to oil-in-water emulsions which contain ionic surfactants based on sulfonates and/or sulfates.

EP-A-062 181 discloses oil-in-water (O/W) emulsions which contain the active substance and also, as emulsifier, at least one but generally more than one alkylaryl polyglycol ether in a mixture with ionic salts of alkylarylsulfonic acids. A disadvantage of these emulsions is the necessity of a surfactant mixture comprising nonionic and ionic surfactants.

EP-A-0 160 182 specifies aqueous microemulsions which contain as active substance a synthetic pyrethroid and as emulsifier a surfactant comprising calcium dodecylsulfonate, ethoxylated distyrylphenolammonium sulfate and ethoxylated tristyrylphenol.

The aqueous emulsion concentrates (EW) described therein necessarily contain a surfactant mixture comprising ionic and nonionic surfactants.

U.S. Pat. No. 2,696,453 describes plant protection formulations which necessarily contain a mixture of a nonionic surfactant, for example isooctylphenol ether with 10–11 mol EO (®Triton X-00) or alkylphenoxyp-olyethoxy-ethanol (®Triton X-155) and an oil-soluble calcium or magnesium salt of an alkylbenzenesulfonic acid. A further disadvantage of these plant protection formulations is to be seen in the high content of organic solvents such as xylene, kerosine and/or naphthalene derivatives, for which values of from 26 to 70% by weight are given.

The object of the present invention was to provide plant protection formulations, in the form of aqueous,-emulsion concentrates based on active substances, especially active substances which are sensitive to hydrolysis, from the group consisting of phosphates, thiophosphates and/or carbamates, which formulations are completely free from organic solvents, have an excellent chemical and physical stability, are resistant in particular to hydrolysis, and are also stable at low temperatures (−10° C.), and which are dilutable with water as desired either alone or in a mixture with other liquid formulations.

It has now surprisingly been found that the use of specific surfactant compounds leads to the desired plant protection formulations. Specifically, these surfactant compounds are A) nonionic surfactant compounds of formula I below,
B) phosphorylated surfactant compounds of formula II below,
C) sulfated surfactant compounds of formula III below, and
D) sulfonated surfactant compounds of formula IV below.

The present invention relates to oil-in-water emulsions comprising:

0.001–70% by weight, preferably 0.5–50% by weight, of at least one active substance from the group consisting of phosphates, thiophosphates and/or carbamates, 0.001–30% by weight, preferably 0.1–20% by weight, of one or more surfactant compounds from the group consisting of A) nonionic surfactant compounds of the formula I

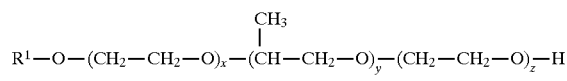

in which
R$^1$ is hydrogen
$C_1$–$C_{24}$-alkyl,
$C_2$–$C_{24}$-alkenyl,
$C_2$–$C_{24}$-alkynyl,
$C_5$–$C_{24}$-cycloalkyl,
$C_6$–$C_{36}$-aryl,
$C_6$–$C_{48}$-alkaryl,
$C_6$–$C_{36}$-heteroaryl or
$C_6$–$C_{48}$-heteroalkaryl,
x and z independently of one another are a number from 0 to 300 and
y is a number from 0 to 200,
with the proviso that the sum of x, y and z is a number greater than zero,
or
B) phosphorylated surfactant compounds of the formula II

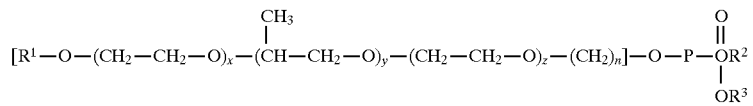

in which

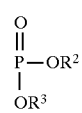

n is a number from 1 to 3
x, y and z are as defined for formula I,
R$^2$ is hydrogen,
an alkali metal cation, one equivalent of an alkaline earth metal ion,
ammonium,
mono-, di- or tri($C_1$–$C_{12}$)alkylammonium or
mono-, di- or tri($C_1$–$C_{12}$)alkanolammonium,
and R$^3$ is R$^2$ or the square-bracketed expression of the formula II, i.e.,

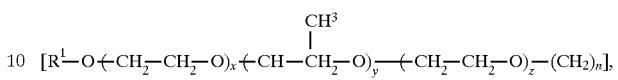

where n is a number from 1 to 3,
or

C) sulfated surfactant compounds of the formula III

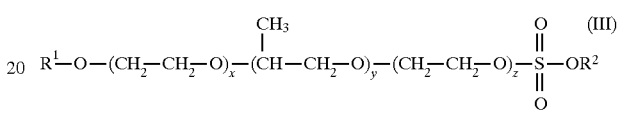

in which

R$^1$ is as defined for formula I or is a radical of the formula

R$^2$ is as defined for formula II, and
x, y and z are as defined for formula I,
or D) sulfonated surfactant compounds of the formula IV

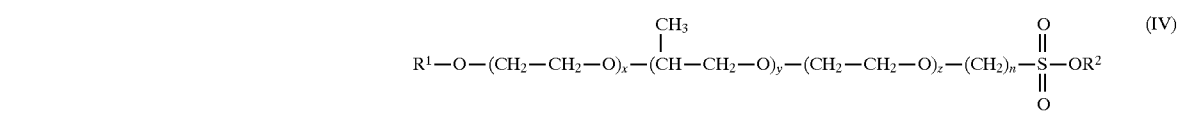

in which
R$^1$ is as defined for formula I,
R$^2$ is as defined for formula II,
x, y and z are as defined for formula I, and
n is a number from 1 to 3, and, if desired, adjuvants and water to make up 100% by weight.

The O/W emulsions according to the invention contain at least one agrochemical active substance, an active substance for controlling harmful organisms in the household and hygiene sector and/or a pharmacologically active substance from the class of the phosphates, thiophosphates and/or carbamates. In this context the active substances, preferably active substances sensitive to hydrolysis, which are suitable include both those substances which are liquid at room temperature and those which are solid at room temperature. Such active substances are known and described, for example, in "The Pesticide Manual" 9th edition, The British Crop Protection Council, 1991.

In the present case the term agrochemical substances is understood to refer to those substances which are usually employed in plant protection. Examples of these include insecticides, acaricides, fungicides, nematicides, herbicides, molluscicides, rodenticides, growth regulators, safeners, adjuvants, fertilizers and algicides.

Specific examples of such active substances are:

O,O-diethyl O-[2-isopropyl-4-methyl-6-pyrimidyl] thiophosphate (diazinon)

O,O-diethyl O-[3,5,6-trichloro-2-pyridyl] thiophosphate (chlorpyrophos)

2-(1-methylpropyl)phenyl methyl carbamate (BPMC)

O,O-dimethyl S-methylcarbamoylmethyl thiophosphate (dimethoate)

chlorobicyclo[3.2.0]hepta-2,6-diene-6-yl phosphate (heptenophos)

O,O-diethyl O-1-phenyl-1H-1,2,4-triazol-3-yl thiophosphate (triazophos)

ethyl 2-diethoxyphosphinothioyloxy-5-methylpyrazolyl [1,5-β]pyrimidine-6-carboxylate (pyrazophos)

O,O-diethyl O-(4-nitrophenyl) thionophosphate

O,O-dimethyl O-(4-nitrophenyl) thionophosphate (fenitrothion)

O-(ethyl O-4-methylthiophenyl S-propyl dithiophosphate 2-isopropoxphenyl N-methylcarbamate 2,3-dihydro-2,2-dimethyl-7-benzofuryl methylcarbamate 3,5-dimethyl-4-methylthiophenyl N-methylcarbamate O,O-diethyl O-(3-chloro-4-methyl-7-coumarinyl) thiophosphate S-[1,2-bis(ethoxycarbonyl) ethyl] O,O-dimethyldithiophosphate (malathion)

O,O-dimethyl O-4-methylmercapto-3-methylphenyl thionophosphate (fenthion, Lebaycid)

O-ethyl O-2-isopropyloxycarbonylphenyl N-isopropylthionophosphoramide.

In the present case, active substances for controlling pests in the household and hygiene sector are to be understood as all conventional active substances of low solubility in water. Specific examples of such active substances are:

2-isopropoxyphenyl N-methylcarbamate

O,O-diethyl O-4-nitrophenyl thionophosphate (ethyl-parathion)

O,O-dimethyl O-4-nitrophenyl thionophosphated (methyl-parathion)

S-[1,2-bis (ethoxycarbonyl) ethyl] O,O-dimethyl dithiophosphate

O,O-dimethyl O-3-methyl-4-nitrophenyl thionophosphate (sumithion, folithion)

O,O-dimethyl O-4-methylmercapto-3-methylphenyl thionophosphate (Lebaycid, fenthion).

In the present case pharmacologically active substances are to be understood as substances of low solubility in water which can be preferably employed in the veterinary sector. An example of such active substances is chlorobicyclo [3.2.0]hepta-2,6-dien-6-ylphosphate (heptenophos).

The formulation according to the invention contain at least one surfactant of formula I, II, III or IV.

In the surfactants of the formula I $R^1$ is preferably hydrogen, $C_{10}$–$C_{18}$-alkyl, $C_2$–$C_{18}$-alkenyl, $C_6$–$C_{20}$-cycloalkyl, $C_6$–$C_{18}$-aryl or $(C_1$–$C_{12}$-alkyl$)_3$-phenyl, especially $C_1$–$C_{12}$-alkylphenyl or mono-, di- or tristyrylphenyl. Tributylphenyl Where the radicals $R^1$ are other than hydrogen they may carry suitable substituents, examples being halogen atoms, alkoxy groups, hydroxyl groups, nitro groups, amino groups and/or carboxyl ester groups.

The indices x, y and z indicate the respective number of moles of ethylene oxide and/or propylene oxide units.

The indices x, y and z have the following preferred ranges:

x and y equal zero, z is a number between 5 and 30;

x is a number between 2 and 45, y is a number between 2 and 35 and z equals zero;

y equals zero, x and z independently of one another are a number between 1 and 60;

x equals zero, y is a number between 2 and 30 and z is a number between 2 and 40.

Further preferred ranges are:

x, y and z independently of one another are numbers between 1 and 120, between 1 and 80 and between 1 and 30.

Of very particular suitability are surfactant compounds of the formula I in which $R^1$ is mono-, di- or tristyrylphenyl, x is a number between 8 and 40, y is a number between 0 and 25, and, z is a number between 0 and 40.

Preferred compounds of the formula I are obtainable under the designation ®Emulsogen 3510, HOE S 2436 and HOE S 1816 (products of Hoechst AG, DE).

The surfactants of the formula I can be prepared in a simple manner. Surfactants of the formula I in which $R^1$ is hydrogen can be prepared by the methods indicated in DE–C-3 542 411. Surfactants of the formula I in which $R^1$ is other than hydrogen are obtained by alkoxylation of the corresponding alcohols of the formula $R^1$-OH by the method indicated in DE–C-3 542 411, to give the surfactants employed in accordance with the invention.

In the surfactants of the formula II $R^1$ is preferably $C_{10}$–$C_{18}$-alkyl, $C_2$–$C_8$-alkenyl, $C_6$–$C_{20}$-aryl, $C_1$–$C_{12}$-alkylphenyl or mono-, di- or tristyrylphenyl or a radical of the formula

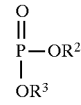

in which $R^2$ and $R^3$ independently of one another are an alkali metal cation, mono-, di- or tri($C_2$–$C_4$-alkyl) ammonium or tri($C_2$–$C_4$-alkanol)ammonium.

The radicals $R^2$ and $R^3$ are preferably an alkali metal cation, mono-, di- or tri($C_2$–$C_4$-alkyl)ammonium or tri($C_2$–$C_4$-alkanol) ammonium.

The preferred ranges for the indices x, y and z are those specified with regard to formula I.

The alkali metal and/or tri($C_2$–$C_4$-alkanol)ammonium-salts are particularly preferred.

Preferred surfactants of the formula II are available under the names HOE S 3475, HOE S 3475-1, HOE S 3475-2 (products of Hoechst AG, DE).

The surfactants of the formula II can be prepared in a simple manner. Surfactants of the formula II in which $R^1$ is hydrogen can be prepared by the methods specified in DE–C-3 542 441. The surfactants of the formula It in which $R^1$ is other than hydrogen are obtained by alkoxylation of the corresponding alcohols of the formula $R^1$-OH to give the corresponding nonionic block copolymers which are reacted by subsequent phosphorylation, in accordance with DE–C-3 542 441, to give the surfactants of the formula II according to the invention.

In the surfactants of the formula III $R^1$ is preferably $C_1C_{18}$-alkyl, $C_2$–$C_{18}$-alkenyl, $C_6$–$C_{20}$-cycloalkyl, $C_1$–$C_{18}$-alkylphenyl, especially 1-phenylethyl or $C_2$–$C_{18}$-alkenylphenyl, in particular styryl or a radical of the formula

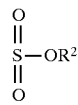

in which $R^2$ is an alkali metal cation, mono-, di- or tri ($C_1$–$C_{12}$-alkyl)ammonium or tri($C_1$–$C_{12}$-alkanol) ammonium.

$R^2$ is preferably an alkali metal cation, mono-, di- or tri($C_1$–$C_{12}$-alkyl)ammonium or tri($C_1$–$C_{12}$-alkanol) ammonium.

$R^2$ is particularly preferably an alkali metal cation, mono-, di- or tri($C_2$–$C_4$-alkyl)ammonium or tri($C_2$–$C_4$-alkanol) ammonium.

The preferred ranges for the indices x, y and z are those specified with regard to formula I.

Very particularly preferred surfactants are the potassium, sodium and triethylammonium salts of 2,4,6-bis(1-phenylethyl)phenyl polyglycol ether sulfate with 20 EO (average value). Suitable surfactants of the formula III are the following products:

®Genapol LRO, ®Hostaphat BV conc. and ®Sapogenat BK conc. (Hoechst AG, DE).

The preparation of the surfactants of the formula III is analogous to the preparation procedure described above. The surfactants according to the invention are obtained by sulfation of the nonionic block copolymers corresponding to the formula I (see K. Kosswig and H. Stache, "Die Tenside" [The Surfactants], Hauser-Verlag 1993, p. 130).

In the surfactants of the formula IV $R^1$ is preferably $C_1$–$C_{18}$-alkyl, $C_2$–$C_{18}$-alkenyl, $C_6$–$C_{20}$-cycloalkyl, $C_1$–$C_{18}$-alkyl-phenyl, especially 1-phenylethyl and $C_2$–$C_{18}$-alkenylphenyl, especially styryl.

$R^2$ is preferably an alkali metal cation, mono-, di- or tri($C_2$–$C_4$-alkyl)ammonium or tri($C_2$–$C_4$-alkanol) ammonium. The preferred ranges for the indices x, y and z are those specified with regard to formula I, and n is preferably the number 2.

The surfactant compounds of the formula IV are prepared by analogy with the preparation procedure described above. By reaction of the nonionic block copolymer corresponding to formula I with thionyl chloride to give the corresponding chloro compound, followed by reaction with sodium sulfite, the surfactants of the formula IV are obtained (see. P. K. K. Hodgson, N. J. Stewart, E. J. Tinley; "Alkylphenylethoxyethanesulphonates", Tenside Detergents 23 (1986), 4, pp. 175–177).

The O/W emulsions according to the invention contain water as continuous phase. In the case of concentrated emulsions the proportion of water is relatively low, whereas the emulsions in the diluted state contain relatively large quantities of water. The oil phase (=disperse phase) is present in the form of finely divided droplets in the aqueous phase, the droplet size being variable within a certain range.

The particle diameter is generally between 0.001 and 10 µm, preferably between 0.01 and 5 µm and in particular between 0.1 and 2 µm.

These O/W emulsions advantageously contain no organic solvents. Therefore they have a high flash point and are of low flammability.

Likewise, they are virtually free from odor and generally have a low toxicity, including phytotoxicity.

Adjuvants which may be present in the oil-in-water emulsions according to the invention are preservatives, low temperature stabilizers, dyes and odor improvers. Examples of preservatives are 2-hydroxybiphenyl, sorbic acid, p-hydroxybenzaldehyde, methyl p-hydroxybenzoate, benzaldehyde, benzoic acid, propyl p-hydroxybenzoate and p-nitrophenol. The content of preservative in the emulsion may be between 0.01 and 1% by weight.

Suitable low temperature stabilizers are glycol, glycerol, polyethylene glycol, sugars and salts such as ammonium sulfate and sodium oleate, the emulsions usually being able to have a content of from 1 to 10% by weight. Examples of dyes are azo dyes and phthalocyanine dyes. Odor improvers which it is possible to employ are perfume oils.

One example of a suitable preparation process for this O/W emulsion is described in EP-A-0 130 370. In principle, however, the two phases can be brought into the desired state by stirring.

The oil-in-water emulsions are distinguished by the fact that they are stable under the conditions prevailing in practice. On long-term storage these emulsions remain unchanged with regard to their physical stability and their content of active substance both at high temperatures (50° C.) and at low temperatures (–5° C., –10° C.). A further advantage is that active substances which are solid or liquid at room temperature can be emulsified with equal success. The mandatory use of glycerol as adjuvant and of organic solvents, especially when solid active substances are employed (cf. EP-A-0 196 463), is not required.

The oil-in-water emulsions according to the invention can be applied either as prepared or after dilution beforehand. In this context their application depends on the concentration of the oil-in-water emulsion and on the particular indication. The emulsion is applied by the conventional methods and thus, for example, by spraying or pouring.

The formulation examples collected in the attached tables are evidence of the broad applicability.

In the following text EO is ethylene oxide, PO is propylene oxide.

Plant protection formulations with surfactants of the formula I:

| | $R^1$ | x | y | z |
|---|---|---|---|---|
| Surfactant A1 | Tristyrylphenyl | 20 | 0 | 0 |
| Surfactant A2 | Hydrogen | 66 | 38 | 66 |
| Surfactant A3 | Hydrogen | 15 | 52 | 15 |
| Surfactant A4 | n-$C_4H_6$ | 2 | 23 | 40 |
| Surfactant A5 | Tributylphenyl | 11 | 0 | 0 |
| Surfactant A6 | Nonylphenyl | 15 | 0 | 0 |
| Surfactant A7 | $C_{16}$–$C_{23}$-alkyl | 10 | 0 | 0 |

Table I shows O/W emulsions according to the invention which are stable for a period of at least 1 month (storage temperature 25° C. and 50° C. respectively).

TABLE I

Example; Data in % by weight, water to 100% by weight

| | A1 | A2 | A3 | A4 | A5 | A6 | A7 | A8 | A9 | A10 | A10 |
|---|---|---|---|---|---|---|---|---|---|---|---|
| Surfactant A1 | 7 | 10 | 10 | | | | | | | | |
| Surfactant A2 | | | | 7 | 7 | 7 | | | | | |
| Surfactant A3 | | | | | | | 7 | | | | |
| Surfactant A4 | | | | | | | | | 7 | | |
| Surfactant A5 | | | | | | | | 7 | | | |
| Surfactant A6 | | | | | | | | | | 7 | |
| Surfactant A7 | | | | | | | | | | | 7 |
| Kelzan S 2%, aqueous | 7 | 7 | 15 | 10 | 12 | 5 | 13.3 | 13.3 | 13.3 | 13.3 | 13.3 |
| Antifoam emulsion SE2 | | | | 1 | 1 | | | | | | |
| Malathion 95–96% | 42 | 42 | 42 | 42 | 42 | | 42 | 42 | 42 | 42 | 42 |
| Ethylparathion 98% | | | | | | 51 | | | | | |

Plant protection formulations with surfactants of the formula II:

| | $R^1$ | x | y | z | $R^2$ | $R^3$ |
|---|---|---|---|---|---|---|
| Surfactant B1 | $\begin{array}{c}P-(O)-OR^2\\|\\OR^3\end{array}$ | 66 | 38 | 66 | H | TEA*) |
| Surfactant B2 | $\begin{array}{c}P(O)-OR^2\\|\\OR^3\end{array}$ | 15 | 52 | 15 | H | TEA |
| Surfactant B3 | n-$C_4H_6$ | 2 | 23 | 40 | H | TEA |
| Surfactant B4 | tri-sec-butyl-phenyl | 11 | 0 | 0 | H | TEA |
| Surfactant B5 | $C_{16}$-alkyl | 10 | 0 | 0 | H | TEA |

TEA = triethanolammonium

Table II shows oil-in-water emulsions according to the invention which are stable for a period of at least 1 month (storage temperature: 25° C.; 50° C.).

TABLE II

Example; Data in % by weight, water to 100% by weight

| | B1 | B2 | B3 | B4 | B5 | B6 | B7 | B8 | B9 | B10 | B11 | B12 | B13 |
|---|---|---|---|---|---|---|---|---|---|---|---|---|---|
| Surfactant B1 | 7 | 7 | 7 | 8 | 7 | | | | | | | | |
| Surfactant B2 | | | | | | 7 | 7 | 7 | 7 | | | | |
| Surfactant B3 | | | | | | | | | | | 7.0 | | |
| Surfactant B4 | | | | | | | | | | | | 7.0 | |
| Surfactant B5 | | | | | | | | | | | | | 7.0 |
| 10% aqueous sodium hydroxide | 1.5 | 1.5 | 1.5 | 1.7 | 1.5 | | | | | 1.7 | | | |
| Triethanolamine | | | | | | 1.07 | 1.07 | 1.07 | 1.07 | | 2.8 | 2.45 | 2.6 |
| Kelzan S 2% aqueous | 8.0 | 5.0 | 13.0 | | 4.0 | 13.3 | | | 23.3 | 8.0 | 14.0 | 13.3 | 13.3 |
| Antifoam emulsion SE2 SE57 | 1.0 | 1.0 | 1.0 | 1.0 | 1.0 | | 1.0 | 1.0 | | | | | |
| Ethylparathion 98% | 51.0 | 51.0 | | | | | | | | 51.0 | | | |
| Malathion 95–96% | | | 42.0 | | | 42.0 | 42.0 | 42.0 | 42.0 | | 42.0 | 42.0 | 42.0 |
| Diazinon 95% | | | | 52.6 | | | | | | | | | |
| Fenitrothion | | | | | 52.1 | | | | | | | | |

| Plant protection formulations with surfactants of the formulae III and IV: | |
| --- | --- |
| Surfactant C1 | Tristyrylphenol polyglycol ether sulfate (about 20 EO) TEA salt |
| Surfactant C2 | Tributylphenol polyglycol ether sulfate (about 8 EO) sodium salt |
| Surfactant C3 | Lauryl diglycol ether sulfate, sodium salt |
| Surfactant D1 | Tristyrylphenol polyglycol ether sulfonate (about 20 EO), TEA salt |

Table III shows O/W emulsions according to the invention which are stable for a period of at least 1 month at 25° C. and are also predominantly stable up to or at 50° C.

TABLE III

| Example; data in % by weight, water to 100% by weight | | | | | | | |
| --- | --- | --- | --- | --- | --- | --- | --- |
| | C1 | C2 | C3 | C4 | C5 | C6 | D1 |
| Surfactant C1 | 7 | 7 | | | | | |
| Surfactant C2 | | | 7 | 7 | | | |
| Surfactant C3 | | | | | 7 | 7 | |
| Surfactant D1 | | | | | | | 5 |
| Kelzan S 2% aqueous | 13 | 13 | 13 | 10 | 13 | 10 | 13 |
| Antifoam emulsion SE 2 | 1 | 1 | | | | | |
| Malathion 95–96% | 42 | | 42 | | 42 | | 42 |
| Ethylparathion 98% | | 51 | | 51 | | 51 | |

We claim:

1. An oil-in-water emulsion which is essentially free from organic solvents and essentially free of glycerol and contains one or more active substances and one or more surfactant compounds, comprising:
   as an active substance, 0.001–70% by weight of a phosphate, a thiophosphate, a carbamate or a mixture thereof;
   as a surfactant, 0.001–30% by weight of at least one nonionic surfactant having structural formula I or at least one sulfonated surfactant having structural formula IV, or nonionic and sulfonated surfactants of the structural formulas I and IV, said structural formulas I and IV being:

$$R^1-O-(CH_2-CH_2-O)_x-(\overset{\underset{\displaystyle CH_3}{|}}{CH}-CH_2-O)_y- \quad (I)$$
$$-(CH_2-CH_2-O)_z-H,$$

$$R^{1d}-O-(CH_2-CH_2-O)_{x3}-(\overset{\underset{\displaystyle CH_3}{|}}{CH}-CH_2-O)_{y3}- \quad (IV)$$
$$-(CH_2-CH_2-O)_{z3}-(CH_2)_n-\overset{\underset{\displaystyle O}{\|}}{\underset{\|}{S}}-OR^{2d}$$

in which
$R^1$ and $R^{1d}$ are $C_1-C_{24}$-alkyl, $C_2-C_{24}$-alkenyl, $C_5-C_{24}$-cycloalkyl, $(C_1-C_{12}$-alkyl$)_3$-phenyl, $C_6-C_{36}$-heteroaryl, or $C_6-C_{48}$-heteroalkaryl,
x, x3, z and z3 independently of one another are a number from 0 to 300,
y and y3 are a number from 0 to 200, with the proviso that the sum of x, y and z or x3, y3 and z3 is a number greater than zero,
$R^{2d}$ is hydrogen, an alkali metal cation, one equivalent of an alkaline earth metal cation, ammonium, mono-, di- or tri-$(C_1-C_{12})$alkylammonium or mono-, di- or tri $(C_1-C_{12})$alkanolammonium and
n is a number from 1 to 3.

2. An oil-in-water emulsion as claimed in claim 1, wherein, in a nonionic surfactant of formula I,
$R^1$ is $C_{10}-C_{18}$-alkyl, $C_2-C_{18}$-alkenyl, $C_2-C_{24}$-alkynyl, $C_6-C_{20}$-cycloalkyl or tributylphenyl.

3. An oil-in-water emulsion as claimed in claim 1, wherein, in a sulfonated surfactant of formula IV, $R^{2d}$ is an alkali metal cation, mono-, di- or tri-$(C_2-C_4$-alkyl) ammonium or tri$(C_2-C_4$-alkanol)ammonium.

4. An oil-in-water emulsion as claimed in claim 1, wherein:
   x, x3, y and y3 equal zero, z and z3 are a number from 5 to 30; or
   x and x3 are a number from 2 to 45, y and y3 are a number from 2 to 35 and z and z3 equal zero; or
   x and x3 are a number from from 1 to 60, y and y3 equal zero and z and z3 is a number from 1 to 60; or
   x and x3 equal zero, y and $y^3$ are a number from 2 to 30 and z and z3 are a number from 2 to 40.

5. An oil-in-water emulsion as claimed in claim 1, wherein x, x3, y, y3, z and z3, independently of one another, are numbers from 1 to 120.

6. An oil-in-water emulsion as claimed in claim 1, which further comprises, as adjuvants, one or more preservatives, low temperature stabilizers, dyes, odor improvers, or a combination thereof.

7. An oil-in-water emulsion as claimed in claim 1, wherein the oil phase of said oil-in-water emulsion comprises a liquid active substance in the form of finely divided droplets, as essentially the oil phase of said oil-in-water emulsion, said droplets being dispersed in the aqueous phase of said oil-in-water emulsion.

8. An oil-in-water emulsion as claimed in claim 7, wherein the diameter of said finely divided droplets ranges from 0.001 to 10 μm.

9. An oil-in-water emulsion as claimed in claim 1, consisting essentially of 0.001–70% by weight of said active substance, 0.001 to 30% by weight of surfactant consisting essentially of said nonionic surfactant or said sulfonated surfactant, and, optionally, one or more preservatives, low temperature stabilizers, dyes, odor improvers, or a combination thereof.

10. An oil-in-water emulsion as claimed in claim 9, wherein the amount of said active substance is 0.5 to 50% by weight, and the amount of said surfactant is 0.1 to 20% by weight.

11. An oil-in-water emulsion which is essentially free of organic solvents and essentially free of glycerol and contains one or more active substances and one or more surfactant compounds, comprising:
   a continuous aqueous phase, and dispersed therein, 0.001–70% by weight of an oil phase, said oil phase consisting essentially of an active substance, liquid at room temperature, which is in the form of finely divided droplets and is a phosphate, a thiophosphate, a carbamate, or a mixture thereof, a surfactant composition consisting essentially of a compound or compounds of only one of the following four structural formulas:

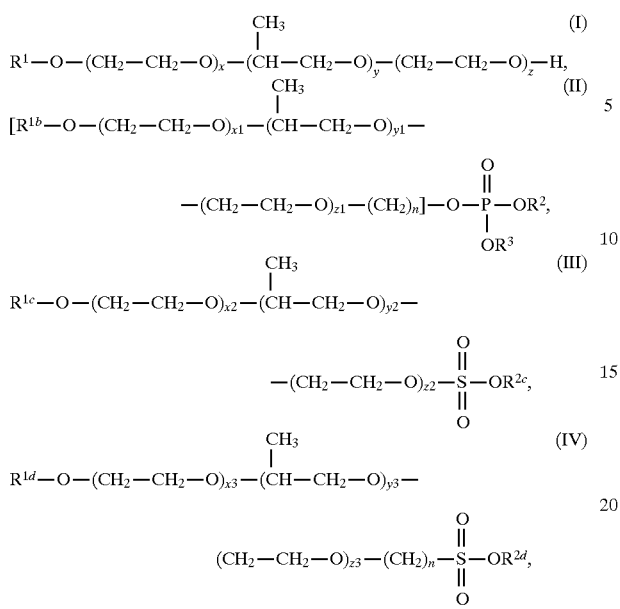

in which

R$^1$, R$^{1b}$, R$^{1c}$ and R$^{1d}$ are hydrogen, C$_1$–C$_{24}$-alkyl, C$_2$–C$_{24}$-alkenyl, C$_2$–C$_{24}$-alkynyl, C$_5$–C$_{24}$-cycloalkyl, (C$_1$–C$_{12}$-alkyl)$_3$-phenyl, C$_6$–C$_{36}$-heteroaryl or C$_6$–C$_{48}$heteroalkaryl, or R$^{1b}$ is a radical of the formula V

R$^{1c}$ is a radical of the formula VI

R$^2$, R$^{2c}$, R$^{2c'}$ and R$^{2d}$ are hydrogen, an alkali metal cation, one equivalent of an alkaline earth metal ion, ammonium, mono-, di- or tri-(C$_1$–C$_{12}$)alkylammonium or mono-, di- or tri(C$_1$–C$_{12}$)alkanolammonium, R$^3$ is defined in the same manner as R$^2$ through R$^{2d}$ or is the square-bracketed expression of said formula II, i.e.

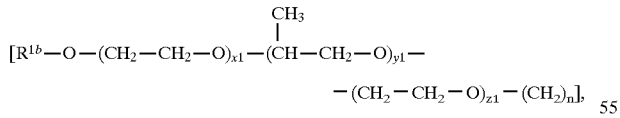

n is a number from 1 to 3, x, x1, x2, x3, z, z1, z2 and z3 independently of one another are a number from 0 to 300, y, y1, y2, and y3 are a number from 0 to 200, with the proviso that the sum of x, y and z or x1, y1 and z1 or x2, y2 and z2 or x3, y3 and z3 is a number greater than zero, and optionally, sufficient water in said aqueous phase and adjuvants to make up 100%.

12. An oil-in-water emulsion as claimed in claim 11, wherein:

x, x1, x2, x3, y, y1 , y2 and y3 equal zero, z, z1 , z2 and z3 are a number from 5 to 30; or x, x1, x2 and x3 are a number from 2 to 45, y, y1, y2 and y3 are a number from 2 to 35 and z, z1, z2 equals zero; or x, x1, x2 and x3 are a-number from from 1 to 60, y, y1, y2, y3 equal zero and z, z1, z2 and z3 is a number from 1 to 60; or x, x1, x2 and x3 equal zero, y, y1, y2 and y3 are a number from 2 to 30 and z, z1, z2 and z3 are a number from 2 to 40.

13. An oil-in-water emulsion as claimed in claim 11, wherein x, x1, x2, x3, y, y1, y2, y3, z, z1, z2 and z3, independently of one another, are numbers from 1 to 120.

14. An oil-in-water emulsion as claimed in claim 11, in which said adjuvant is one or more preservatives, low temperature stabilizers, dyes, odor improvers, or a combination thereof.

15. An oil-in-water emulsion as claimed in claim 11, wherein the diameter of said finely divided droplets ranges from 0.001 to 10 μm.

16. An oil-in-water emulsion as claimed in claim 11, wherein the amount of said active substance is 0.5 to 50% by weight, and the amount of said surfactant composition is 0.1 to 20% by weight.

17. An oil-in-water emulsion as claimed in claim 11, wherein R$^1$, R$^{1b}$, R$^{1c}$ and R$^{1d}$ are hydrogen, C$_{10–C18}$-alkyl, C$_2$–C$_{18}$-alkenyl, C$_6$–C$_{20}$-cycloalkyl or tributylphenyl, or R$^{1b}$ is a radical of the formula V or R$^{1c}$ is a radical of the formula VI, and wherein R$^2$, R$^{2d}$ and R$^3$ independently of one another are an alkali metal cation, mono-, di-, or tri(C$_2$–C$_4$)alkylammonium or tri(C$_2$–C$_4$-alkanol) ammonium, and R$^{2c}$ or R$^{2c'}$ is an alkali metal cation, mono-, di- or tri(C$_1$–C$_{12}$)alkylammonium or tri(C$_1$–C$_{12}$-alkanol) ammonium.

18. An oil-in-water emulsion as claimed in claim 11, wherein x, x1, x2, x3, y, y1, y2, y3, z, z1, z2 and z3, independently of one another, are numbers from 1 to 30.

19. A method for protecting plants comprising the step of applying to said plants an oil-in-water emulsion as claimed in claim 11.

20. A method as claimed in claim 19, wherein said method assists in the control of organisms harmful to the plants.

* * * * *